US007082839B2

(12) United States Patent  
Pyle et al.

(10) Patent No.: US 7,082,839 B2  
(45) Date of Patent: Aug. 1, 2006

(54) APPARATUS AND METHOD FOR TESTING MOISTURE SUSCEPTIBILITY, RUTTING AND FATIGUE OF MATERIAL

(75) Inventors: Roger A. Pyle, Clarion, PA (US); E. Frank Dalton, Mercer, PA (US)

(73) Assignee: Pine Instrument Company, Grove City, PA (US)

( * ) Notice: Subject to any disclaimer, the term of this patent is extended or adjusted under 35 U.S.C. 154(b) by 224 days.

(21) Appl. No.: 10/264,826

(22) Filed: Oct. 4, 2002

(65) Prior Publication Data

US 2003/0140707 A1 Jul. 31, 2003

Related U.S. Application Data

(60) Provisional application No. 60/352,459, filed on Jan. 28, 2002.

(51) Int. Cl.  
*G01N 3/32* (2006.01)

(52) U.S. Cl. ........................................................ 73/808

(58) Field of Classification Search .................. 73/808, 73/150 A, 7, 95.5, 158, 829, 862, 392, 789; 29/445; 324/206; 198/718; 242/544, 417  
See application file for complete search history.

(56) References Cited

U.S. PATENT DOCUMENTS 2,287,148 A 6/1942 Taber (Continued)

FOREIGN PATENT DOCUMENTS

DE 80 08909 4/1980

(Continued)

OTHER PUBLICATIONS

International Search Report.

(Continued)

*Primary Examiner*—Max Noori  
*Assistant Examiner*—Octavia Davis  
(74) *Attorney, Agent, or Firm*—Roetzel & Andress

(57) ABSTRACT

The moisture susceptibility material testing apparatus includes a specimen chuck, multiple rollers, a temperature controlled water bath, and a control system to automate the testing cycle and collection of data. The water bath is prepared at the desired testing temperature. A material specimen, such as a cylindrical hot mix asphalt (HMA) material specimen, is placed within the water bath on multiple rollers and a specimen chuck then clamps the specimen with an adjustable force. A first and second roller are positioned about the exterior circumference of the cylindrical specimen and a predetermined force is applied radially to the specimen through a third roller. The specimen is rotated about its cylindrical axis, driven by the rotation of the rollers and specimen chuck. A displacement sensor monitors the position of the third roller, yielding a measurement of the rut depth on the material specimen. The number of revolutions the specimen experiences while the force is applied and the rut depth are recorded during the test. Test temperature and rotational velocity are also recorded. Once the third roller has reached a specified displacement (rut depth), or a specified number of force repetitions have occurred, the test is complete. The roller displacement (rut depth) vs. the number of force repetitions is graphed. Test temperature and rotational velocity are also recorded. The resulting data yields information on the effect of moisture on the durability of the HMA product. If desired for comparison purposes, the test may be repeated dry within a temperature-controlled chamber. The apparatus and method may also be used to evaluate rutting and fatigue failure mechanisms in cylindrical material specimens.

19 Claims, 5 Drawing Sheets

U.S. PATENT DOCUMENTS

| | | | | |
|---|---|---|---|---|
| 2,920,481 | A | | 1/1960 | Hulswit, Jr. et al. |
| 3,119,257 | A | | 1/1964 | Speer |
| 3,640,127 | A | * | 2/1972 | Meissner ..................... 73/95.5 |
| 3,854,323 | A | | 12/1974 | Hearn et al. |
| 3,881,346 | A | * | 5/1975 | Scheucher ................. 73/95.5 |
| 4,452,065 | A | * | 6/1984 | Minter ............................ 73/7 |
| 4,502,327 | A | | 3/1985 | Scrivener et al. |
| 4,887,343 | A | * | 12/1989 | Ohishi ......................... 29/445 |
| 4,887,463 | A | | 12/1989 | Wood |
| 4,938,055 | A | | 7/1990 | Tsuda |
| 5,005,778 | A | * | 4/1991 | Gladish ....................... 242/544 |
| 5,344,089 | A | * | 9/1994 | Crowley et al. ............ 242/417 |
| 5,365,793 | A | | 11/1994 | Terrel et al. |
| 5,641,901 | A | | 6/1997 | Powell |
| 5,659,140 | A | | 8/1997 | Jakob et al. |
| 5,837,882 | A | * | 11/1998 | Bacigalupo et al. ............. 73/7 |
| 5,936,398 | A | * | 8/1999 | Bellefeuille ................. 324/206 |
| 5,969,261 | A | | 10/1999 | McAlister et al. |
| 5,987,961 | A | | 11/1999 | Harris et al. |
| 6,125,685 | A | | 10/2000 | Collier et al. |
| 6,427,541 | B1 | * | 8/2002 | Kalin et al. .................... 73/829 |
| 6,550,323 | B1 | * | 4/2003 | Nguyen et al. ................ 73/158 |
| 6,612,189 | B1 | * | 9/2003 | Miyauchi ............... 73/862.392 |

FOREIGN PATENT DOCUMENTS

| | | |
|---|---|---|
| DE | 93 15 832 U | 2/1994 |
| FI | 890359 | 3/1991 |

OTHER PUBLICATIONS

"Test Equipment for the World's Highways", Wessex Engineering Ltd., viewed on Oct. 7, 2002, pp. 1-2, http://www.wessexengineering.co.uk/product1.asp.

"Oder: 4 Years Along the Road with Sasobit", Experiences with Sasobit in 4 Years, pp. 1-5.

"Minutes of the Third Meeting of the Four State Pavement Pooled Fund Study", last viewed on Sep. 18, 2002, pp. 1-18, http://pavements.ce.washington.edu/sptc/austin.asp.

"Tests that Predict Pavement Performance Show the Benefits of PMAs made with Elvaloy RET", DuPont Elvaloy RET, last viewed on Sep. 18, 2002, pp. 1-3, http://www.dupont.com/asphalt/link4.html.

Cooley, Allen L. Jr., et al., "Loaded Wheel Testers in the United States: State of the Practice", NCAT Report No. 2000-4, Jul. 2000, pp. 1-26.

Brown, Ray E., et al., "Performance Testing for Hot Mix Asphalt (Executive Summary)", NCAT Report No. 2001-05A, Nov. 2001, pp. 1-10.

Kandhal, Prithvi S., et al., "Characterization Tests for Mineral Fillers Related to Performance of Asphalt Paving Mixtures", NCAT Report No. 98-2, Jan. 1998, pp. 1-26.

"Asphalt Testing-Mix (Superpave)", Construction Materials Technology Network, Oct. 7, 2002, pp. 1-3, http://www.qcqa.com/product/product.asp?prodpid=250.

"Hamburg Wheel Tracking", Koch Pavement Solutions, Last viewed on Sep. 18, 2002, pp. 1-3, http://www.kochpavementsolutions.com/Solutions/hamburg.htm.

"Are All PG 70-22's The Same? Lab Tests on Kentucky 1-64 Field Samples", Koch Pavement Solutions, Last viewed on Oct. 7, 2002, pp. 1-4, http://www.kochpavementsolutions.com/case_studies/gp_7622s.htm.

"Advanced Asphalt Testing Laboratory", KAPAASPHLAB, Last viewed on Oct. 7, 2002, pp. 1-6, http://www.ksu.edu/pavements/asphtLab.html.

Blankenship, Phillip B., et al. "Experiences with Superpave Volumetric Mix Designs", Last viewed on Oct. 7, 2002, pp. 1-2, http://www.utexas.edu/research/superpave/articles/koch2.html.

Guericke, Rolf, English Version of a publication in the German magazine BITUMEN, Jan. 2001, p. 1-16, http://www.arbit.de/html/english/default.htm.

"Summary of FHWA SHRP Mixtures Expert Task Group Meeting", Asphalt Institute Division of Research Memorandum, Last viewed on Oct. 7, 2002, pp. 1-3, http://www.asphaltinstitute.org/airesear/mixeta97.html.

Chapter 2: Validation of the Superpave Binder Parameter for Rutting based on Alf Pavement Tests at 58 C, pp. 31-72.

Chapter 3: Validation of the Superpave Binder Parameter for Rutting based on Alf Pavement Performance at all Test Temperatures, pp. 73-117.

Chapter 4: Validation of Laboratory Mixture Tests for Rutting Susceptibility, pp. 118-190.

Chapter 5: Effect of Compaction Method on Rutting Susceptibility, pp. 191-215.

"Validation of Asphalt Binder and Mixture Tests That Measure Rutting Susceptibility", U.S. Department of Transportation, Nov. 2000, pp. 1-30.

"S810—Wet Wheel Tracker", Wessex Engineering Ltd., Last viewed on Oct. 7, 2002, http://www.wessexengineering.co.uk/further.info.html.

"Immersion Wheel Tracker S810", Wessex Engineering Ltd., pp. 1-8.

"Wessex Wheel Tracker Specification S867", Wessex Engineering Ltd., pp. 1-35.

"Immersion Wheel Tracker", Wessex Engineering Ltd., pp. 1-8.

"Transportation System Performance", Mack-Blackwell Transportation Center, Last viewed on Sep. 18, 2002, pp. 1-4, http://www.mackblackwell.org/research/frintro.html.

"Wheel Test makes Tracks", Asphalt Contractor, Last viewed on Oct. 7, 2002, pp. 1-4, http://www.asphalt.com/equipment/wheel.html.

"Durability by Design", Last viewed on Sep. 18, 2002, pp. 1-3, http://www.mdasphalt.org/paver98/cecil.html.

"Section 37. Tex-242-F, Hamburg Wheel-tracking Test", Manual of Testing Procedures, pp. 1-5.

"Hamburg Wheel-Track Testing of Compacted Bituminous Mixtures", Colorado Procedure L 5112, Jun. 14, 2002, pp. 1-5.

"Evaluator of Rutting and Stripping in Asphalt Pavements", Challenge Technology, Material Testing Division, pp. 1-4.

Rand, P.E., Dale A., "HMA Moisture Sensitivity Past, Present & Future", TxDOT Experiences, Power Point Presentation pp. 1-43.

Cooley Jr., Allen L., et al., "Loaded Wheel Testers in the United States: State of the Practice", Transportation Research E-Circular, Jul. 2000, No. E-C016, pp. 1-19.

NCAT Activities, Power Point Presentation, Feb. 2002, pp. 1-54.

"PMW's Wheel Tracking Machine", Asphalt Contractor, Last viewed on Oct. 7, 2002, pp. 1-2, http://www.asphalt.com/HHIW/wheel.html.

King, Gayle, "Moisture Damage? The Majestic Matters!", WRI Workshop Moisture Damage, Jul. 2002, pp. 1-38.

Spurbildungsversuch nach TPA-StB, Last viewed on Oct. 7, 2002, pp. 1-2, http://wbserver.bau.uni-wuppertal.de/spur.htm.

"Spurrinnenbildung", Baustoffe—Anwendungen, Last viewed on Oct. 7, 2002, pp. 1-2, http://www.ifm-dr-schellenberg.de/baustoffe_anwendungen_1.htm.

"European Asphalt Study Tour", Report on the 1990, pp. 1-109.

"Full Product Line", Pavement Technology, pp. 1-8.

"The Tracker", Cooper Research Technology makes Wheel Tracking Simple With . . . , pp. 1-2.

Guericke, R., et al, "Results of ARBIT Test Programme 1998/99 Involving 36 Unmodified and Modified Bituminous Binders on the German Market", Eurasphalt & Eurobitume Congress 2000 in Barcelona, pp. 1-48.

"Bituminous Materials", Toni Technik, p. 67.

"Splittmastixasphalt", Asphalt Leitfaden, pp. 1-31.

Williams, Stacy Goad, "Development of Wheel-Tracking Test method and performance Criteria for Asphalt Pavements", Dec. 2001, pp. 1-350.

Rand, Dale, et al., "Evaluate the Fatigue Resistance of Rut Resistant Mixes", Research Project Statement, Jan. 4, 2002, pp. 1-3.

* cited by examiner

APPARATUS AND METHOD FOR TESTING MOISTURE SUSCEPTIBILITY, RUTTING AND FATIGUE OF MATERIAL

This application claims the benefit of Provisional Application No. 60/352,459, filed on Jan. 8, 2002.

FIELD OF THE INVENTION

This invention relates, in general, to the relative measurement of the susceptibility of any type of moldable material, including hot mix asphalt (HMA) to moisture damage and to the relative measurement of rutting and fatigue.

BACKGROUND OF THE INVENTION

Moisture induced damage is a significant problem on society's transportation infrastructure including roads and bridges. Hot Mix Asphalt (HMA) is commonly used as a construction material on these structures because of its relatively low initial cost and low repair costs over alternate materials. While the HMA is in service on these structures, it is exposed to a variety of weathering elements including moisture. Moisture induced damage can cause large rehabilitation and repair expenses and cause significant inconvenience to the public while roads and structures are closed for repairs.

One failure mechanism that plays a part in the destruction of the HMA material is the degradation of the bond between the asphalt binder and the aggregate materials caused by moisture. This degradation, more commonly referred to as stripping, can cause a variety of problems in the HMA structure. Stripping is the failure of the adhesion between the aggregate and asphalt cement binder in HMA. Stripping occurs when water gets between the asphalt binder and the aggregate surface, and/or when water interacts with the asphalt binder and reduces its cohesive properties. Factors that influence the occurrence and severity of stripping include physical and chemical properties of both the aggregate and asphalt cement and the environment in which the pavement exists. The combination of temperature, water, and the shearing force applied by tires is a likely cause for stripping. It is therefore important to obtain an accurate measure of the resistance to stripping as a critical part of evaluating the HMA concrete material properties. If moisture susceptibility can be detected early in the design phase of the HMA construction cycle, precautions can be taken to reduce the susceptibility to stripping in the field, such as adding chemical anti-stripping agents to the HMA mixture. However, these anti-stripping agents add cost to the mixture, so unnecessary use of such agents is undesirable.

Several tests currently exist for evaluating the susceptibility of the HMA to stripping damage, however, each test has its shortcomings. These shortcomings include inconsistent results, large bulky testing equipment, long testing times, time consuming specimen preparation and conditioning, etc. Most of the strength/modulus type tests available simply look at "conditioned vs. unconditioned", an approach that may not yield the desired results. Many of the current devices also require specialized specimen preparation equipment and procedures. Some existing reciprocating type material testing machines utilize a crank-arm system to move the load across the specimen and therefore provide a sinusoidal velocity profile rather than a constant velocity loading profile.

SUMMARY OF THE INVENTION

The device includes a specimen chuck capable of allowing a cylindrical specimen to rotate about its major axis. The specimen is placed into the chuck and centered axially to the rollers by adjusting the position of the chuck clamping faces. The specimen chuck then rotates along with the specimen about an axis that is parallel with the roller axes. The rotation rate can vary from zero or near zero for creep-like measurements, to very fast to reduce testing time for fatigue measurements. The specimen chuck provides a small adjustable clamping force to hold the specimen in position.

The first and second rollers are mounted with their axes parallel to the specimen axis while the specimen outer diameter is in contact with the rollers. A third, movable roller (or "test roller") is then brought into contact with the specimen, its axis also parallel to the specimen axis. A force, which is applied by any means to the third roller, is subsequently transferred to the specimen. The resulting reaction of the specimen onto the first and second rollers creates an equilibrium condition in which the resulting normal forces from all the rollers are approximately equal, with the exception of the first and second rollers carrying the additional force from the weight of the specimen. If desired, this can be overcome by orienting the specimen axis and the roller axes with a vertical orientation. The rollers are rotationally driven by an electric motor or any other means. The rotational velocity can be constant or varied to simulate different dynamic loading conditions. The first and second rollers in conjunction with the third roller cause the forces acting on any point on the specimen circumference to vary from zero to full load as the specimen rotates. This results in a dynamic force response on the material specimen from a static force application. In addition, the circumference of the specimen acts as though it is a continuous material sample, eliminating the undesirable effect of the rollers traveling onto then off the specimen edges, which is a shortcoming many of the existing devices have. This edge effect loading can cause degradation at the edges not representative of actual performance. Some rut testing machines utilize a slab of material to avoid this edge effect condition, which requires specialized specimen preparation equipment and materials. Utilizing a cylindrical specimen avoids this inconvenience. The circumference of the cylindrical specimen can be held at a constant velocity creating a constant surface velocity force application or, alternatively, a constant loading rate (cycles per minute) can be maintained. This apparatus overcomes some of these shortcomings by providing a means for evaluating moisture susceptibility with an economical, compact device that utilizes cylindrical HMA specimens and provides a high number of force cycles in a short period of time. The cylindrical specimens may be made with a gyratory compactor, cored directly from a pavement area, or manufactured with any suitable compaction device.

A displacement sensor is mounted in a position that permits the measurement of the third or test roller position throughout a test. The position of the roller is recorded as the specimen is rotated giving an indication of the depth of rut in the specimen. The test proceeds until a predetermined amount of displacement of the third or test roller has occurred (rut depth) or a predetermined number of load cycles, or specimen rotations, have been completed.

The rollers may be made of a hard material, such as hardened steel for more severe testing at higher forces, or may be made from a softer, more pliable material for less severe evaluations. Pneumatic rollers with changeable pressure can also be used to simulate specific traffic conditions. The roller width and interface surface geometry can also be used to vary the loading characteristic on the specimen. The roller faces may be crowned, flat faced, treaded, or sharp edged to create a variety of loading conditions. A gearmotor can be used to drive all the rollers simultaneously through a set of toothed belts and pulleys while the specimen is completely submerged in a temperature controlled water bath. With the proper selection of roller material and face geometry, the abrasion resistance and/or surface frictional characteristics of the specimen material can also be investigated under wet or dry conditions. The material being tested determines the selection of roller face geometry. Hard materials typically use a sharper, more aggressive roller face, while softer materials utilize wide roller faces to distribute the force over a greater area.

The control system maintains a constant or variable rotational speed until the test is completed. Each of the rollers can be instrumented with sensors for rotational speed and position data, and for position relative to the specimen. The control system automatically records the position(s) of one or more of the rollers throughout the test. Rotation of the first and second rollers may be monitored with a rotation sensor on the gearmotor. The control system automatically compensates for the change in specimen diameter as the test progresses by using the roller position measurement to calculate the effective specimen diameter. With this compensation calculation, accurate information of the specimen rotation is possible by monitoring the rotation of the rollers and rut depth. Alternately, a sensor, integrally mounted in the specimen chuck, detects each rotation of the specimen while the control system records each rotation along with the corresponding rut depth. The control system stops the test automatically at a predetermined number of specimen rotations, specimen rut depth, or upon complete specimen failure. Specimen rut depth can be monitored or measured at the specimen interface with any of the rollers The specimen rotation sensor when used in conjunction with roller rotation measurement can be used to determine the frictional properties of the specimen, either in a wet condition or dry condition and with different roller face materials. The abrasion resistance of the specimen can also be quantified in a similar manner. The specimen diameter is known through the loading frame position sensor. The rotational speed of the rollers is known through a roller rotation measurement sensor. The specimen rotational speed is known from the specimen rotation sensor. The difference between the actual specimen rotation and that expected from the specimen diameter and roller speed indicates the amount of slippage between the specimen and rollers.

The specimen can be submerged in a temperature controlled water bath or subjected to dry loading. When run submerged, the specimen is typically preconditioned by submersion for a period of time prior to applying the force. This preconditioning can be accomplished directly in the apparatus or in a separate temperature controlled reservoir.

For moisture susceptibility tests of HMA specimens, it can be desirable to run a comparison test with the sample dry. An environmental chamber can be included as an integral part of the apparatus to facilitate temperature control during such testing. Degradation of the bond between the asphalt binder and aggregate materials caused by moisture will show as a large rut depth over a small number of load cycles when submerged in the water bath, while the same materials will have a smaller rut depth over the same number of load cycles while dry. The ratio of the rut depths (wet vs. dry) can be used to quantify the material susceptibility to moisture degradation and may be used as an indicator of the need for chemical modifiers.

DETAILED DESCRIPTION OF PREFERRED AND ALTERNATE EMBODIMENTS

Figure 1:
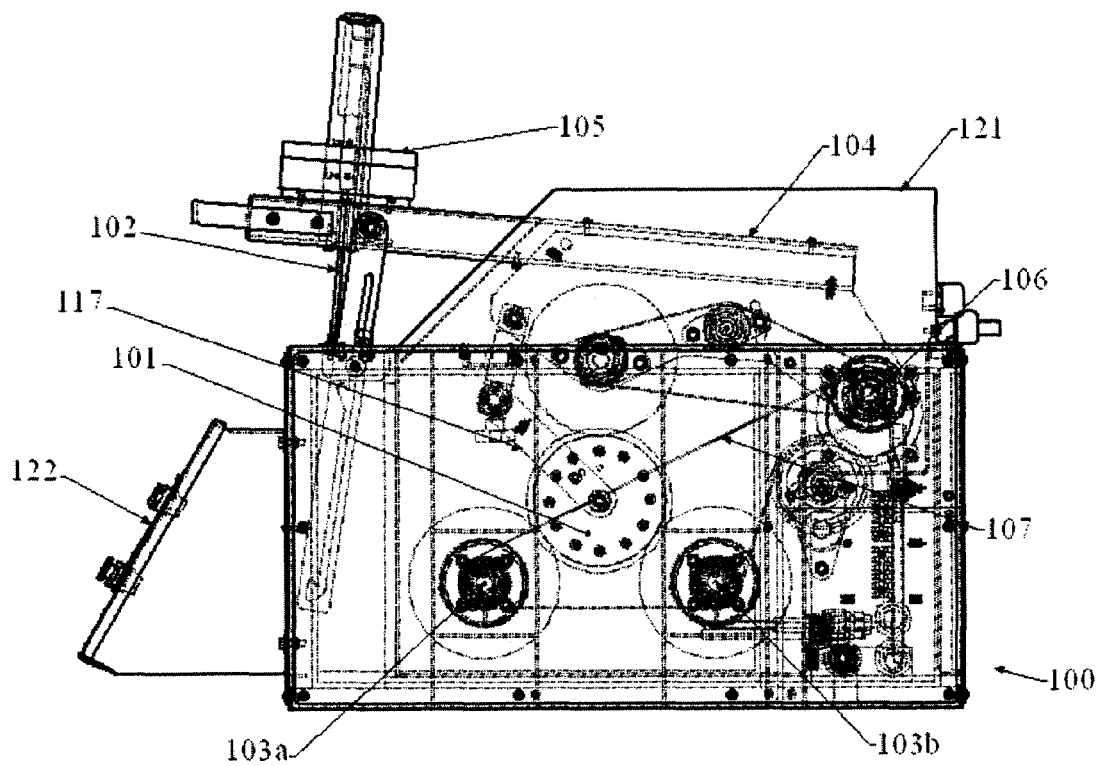
FIG. 1 represents a side view of a representative embodiment of a moisture susceptibility material testing apparatus of the invention.
Figure 2:
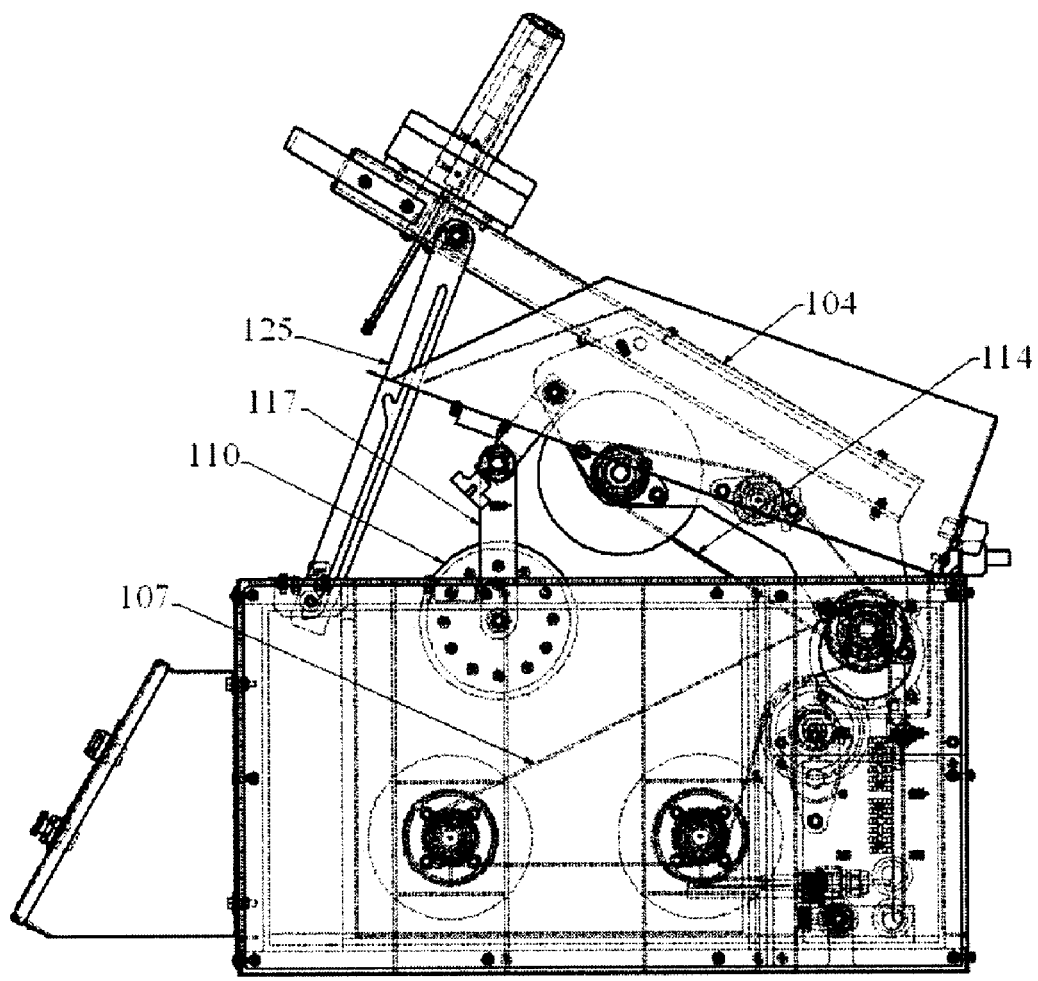
FIG. 2 represents a side view of the apparatus of FIG. 1 with the loading frame and material specimen raised.
Figure 3:
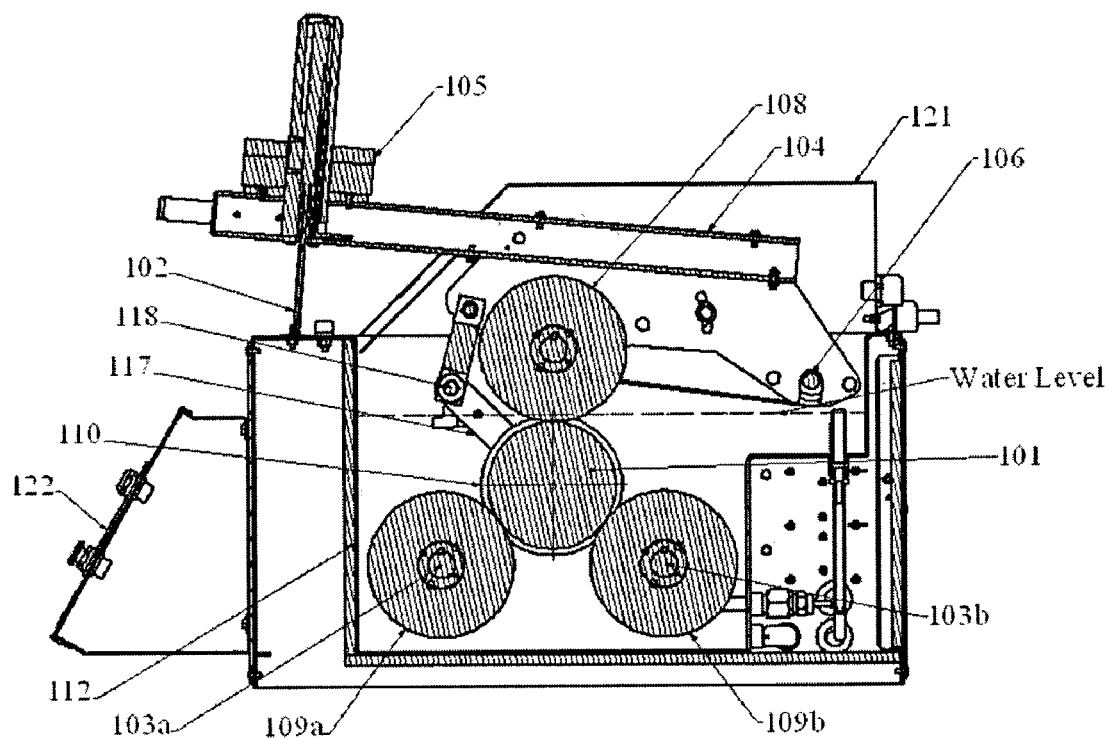
FIG. 3 represents a side cross sectional view of the apparatus of FIG. 1 and a material specimen.
Figure 4:
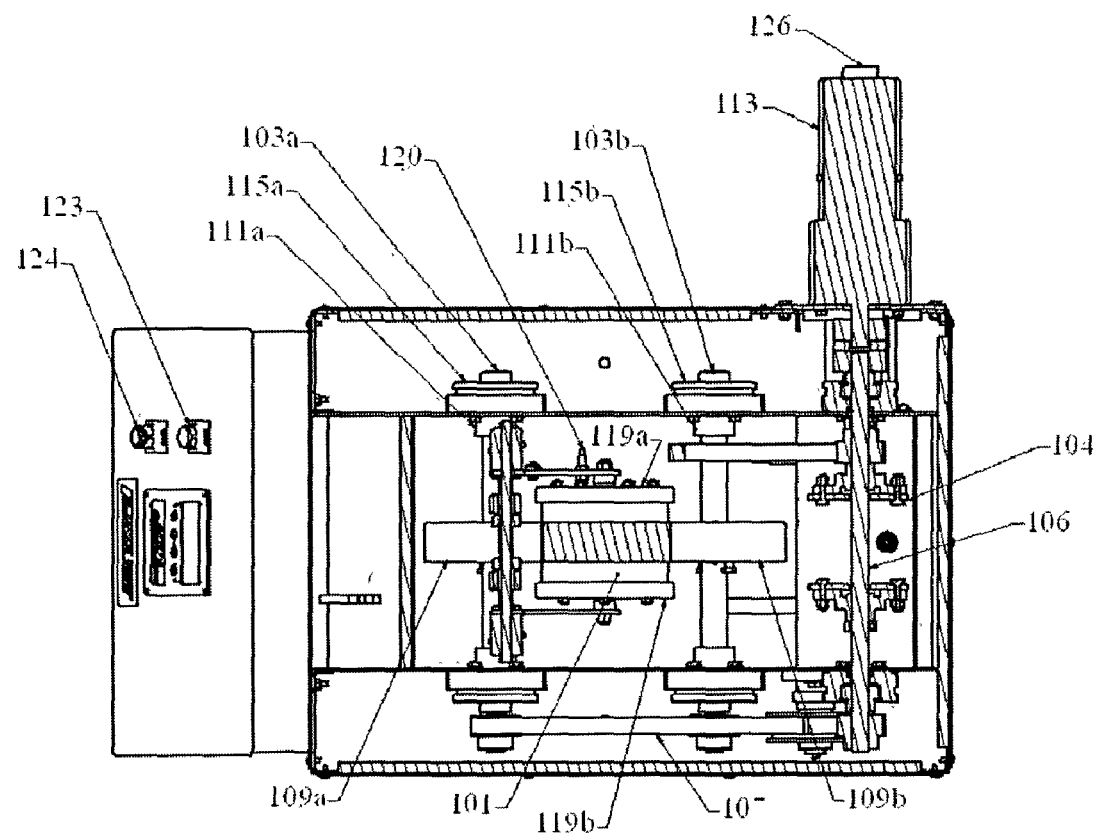
FIG. 4 represents a top cross sectional view of the apparatus of FIG. 1 and a material specimen.

FIGS. 1 through 4 show one example of a cylindrical specimen testing apparatus constructed in accordance with the principles and concepts of the invention. FIG. 1 shows a representation of a side view of the apparatus 100. FIG. 2 shows the apparatus with the loading frame (104) raised. FIG. 3 shows a cross sectional side view of the apparatus with the material specimen (101) in position on the rollers. A gearmotor (113) (shown in FIG. 4) drives the first and second rollers (109a, 109b) (also referred to singularly or collectively as a "reaction roller") through a toothed drive belt (107). A second drive belt (114) is utilized to provide power to the third roller (108). In this embodiment, all rollers are driven at the same rotational velocity and are of the same diameter. The main drive shaft (106) also functions as a pivot to permit raising the loading frame (104) for access to the material specimen (101), specimen chuck (110), and rollers (108, 109a, 109b). First and second rollers (109a, 109b) position the specimen (101) while the third roller (108) is placed onto the specimen (101). The spacing of the first and second rollers (109a, 109b) and third roller (108) around the perimeter of the specimen (101) is such that load sharing of the rollers creates nearly equal forces onto the material specimen at each roller. Only the mass of the specimen (101) causes the forces applied at the first and second rollers (109a, 109b) to be slightly more than the third roller (108) force. The specimen (101) is typically completely submersed in an insulated water bath (112) maintained at a constant temperature, usually 122° F. (50° C.) during the test. However, alternate temperatures may be used that may be more appropriate for the material being tested. The test may also be run dry. The first and second roller shafts are supported by bearings (115a,b), which are mounted to the integral frame/water bath structure. Shaft seals (111a, 111b) where the roller shafts (103a, 103b) enter and exit the water bath (112) prevent leakage of the fluid.

The specimen chuck (110) consists of two rotating disks (119a, 119b) supported by a linkage (117) attached adjustably to a support shaft (118). The rotating disks (119a, 119b) are positioned so as to center the specimen (101) on the rollers (109a, 109b) and provide a means for accommodating various length specimens (101). A specimen rotation sensor (120) is integrated into the linkage (117) supporting the rotating disks (119a, 119b). The first and second rollers (109a, 109b) and third roller (108) can be used with a variety of diameter specimens. Also, different diameter rollers can be installed to provide for a larger variation in specimen diameter than could be accommodated with a single sized set of rollers. A roller rotation measurement sensor (126) is mounted to the gearmotor (113).

Prior to the test, the specimen is typically pre-conditioned in a separate water bath until saturated and at a uniform, stable testing temperature. The specimen may also be pre-conditioned in the apparatus. The support rod (125) supports the loading frame in the raised position. With the loading frame (104) raised, the specimen (101) is transferred from the pre-conditioning bath to the testing apparatus (100) and placed into the specimen chuck (110). Once the specimen is properly centered, the loading frame (104) is lowered bringing the specimen (101) into contact with the first and second rollers (109a, 109b) while the third roller (108) is positioned on the specimen. The desired amount of weight (105) is placed onto the loading frame. A start button (123) initiates the testing sequence and the gearmotor (113) rotates the rollers (108, 109*a*, 109*b*). The specimen (101) is rotated by its intimate contact with all the rollers. The number of load cycles is recorded with rotation sensor (120) and the load roller (108) position is measured with displacement sensor (102) and recorded. Once the desired number of load cycles (specimen rotations) has occurred or the maximum permissible rut depth has been reached, the testing sequence is automatically stopped. A stop button (124) allows the test to be paused or halted at anytime by the operator.

Figure 5:
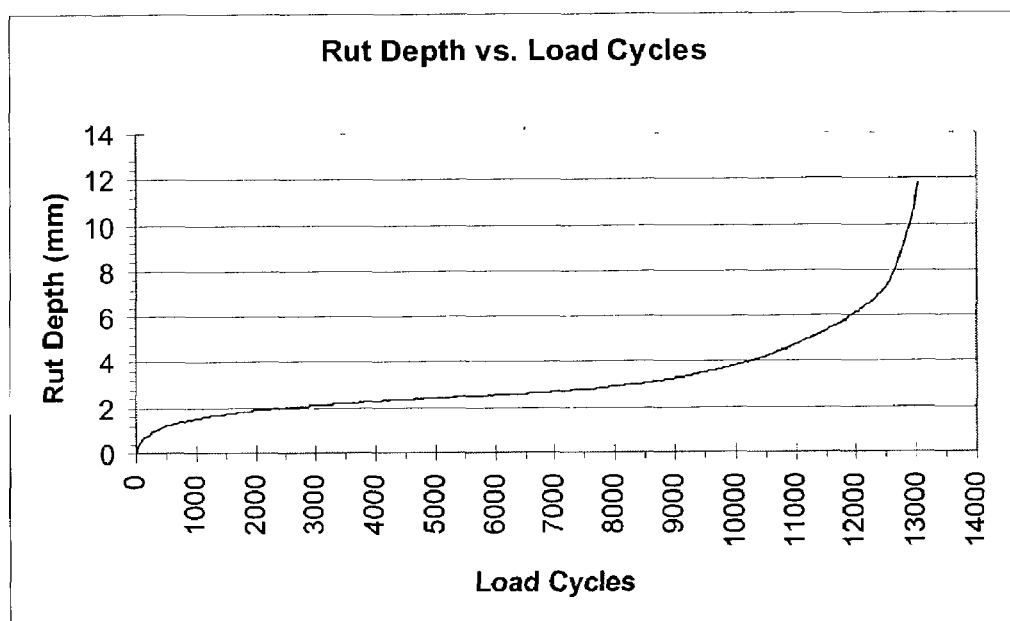
FIG. 5 represents a sample graph of test data producible by the apparatus of the invention.

FIG. 5 shows test data, stored by the control system, plotted as a graph of rut depth vs. load cycles. A relative high rut depth over a low number of load cycles indicates a weak material while a relative low rut depth over a high number of load cycles indicates a stronger material. Catastrophic failure may occur if the specimen splits apart, failing completely during the test. Test temperature and loading rate may also be recorded.

The Figures depict the invention with a loading frame raised manually by the operator but it is within the scope of this invention to include a powered lift mechanism to automatically raise and lower the loading frame. The automatic lift would retract completely allowing the dead weights to provide accurate loading. This mechanism could be an electric screw jack, hydraulic or pneumatic cylinder, and electric motor or otherwise powered device, which raises the loading frame to the open position. The lift mechanism could also be used to apply known forces as an alternative to dead weights. With an automatic lift mechanism, a control system timer may be utilized to automatically apply a set preconditioning time, apply the force, and then raise the frame after the test has run to completion automatically. This feature would provide an accurate preconditioning time as well as adding convenience to the operation of the apparatus.

Although the invention has been shown and described with respect to certain preferred embodiments, certain variations and modifications may occur to those skilled in the art. For example, many different types of motors and drive assemblies could be used to drive the various components and apply various forces to the material specimen through a plurality of rollers. Many different types of control systems could also be employed. Additional rollers may be employed at different locations for contact with the specimen. Alternately, the specimen could be held stationary while the rollers are orbited about the specimen circumference. The apparatus may be used to test materials other than asphalt and asphalt aggregates. All such variations and modifications of the apparatus and method are within the purview of the present invention notwithstanding the defining limitations of the accompanying claims and equivalents thereof.

What is claimed as the invention is:

1. A material testing apparatus comprising:
   a support structure;
   first and second rollers mounted for rotational contact with a material specimen;
   a third roller mounted for applying a radial force to the material specimen;
   a drive system for rotating one of the rollers to rotate the material specimen while said force is applied; and
   a specimen water bath.

2. A material testing apparatus comprising:
   a support structure;
   first and second rollers mounted for rotational contact with a material specimen;
   a third roller mounted for applying a radial force to the material specimen;
   a drive system for rotating one of the rollers to rotate the material specimen while said force is applied; and
   an environmental chamber at least partially surrounding the specimen.

3. A material testing apparatus comprising:
   a support structure;
   at least one roller mounted on the support structure for rotational contact with a cylindrical specimen;
   a test roller mounted for rotational contact with a cylindrical specimen and for applying a radial force to said cylindrical specimen,
   a drive system for driving one of the rollers and rotating said specimen, and a specimen water bath.

4. The apparatus of claim 3 further comprising roller position measurement instrumentation.

5. The apparatus of claim 3 further comprising roller rotation measurement instrumentation.

6. The apparatus of claim 3 further comprising specimen rotation measurement instrumentation.

7. The apparatus of claim 3 further comprising a control system capable of automatically stopping the test at the completion of a specified number of specimen load cycles or a predetermined roller position.

8. The apparatus of claim 3 further comprising means for measuring specimen rotation by combined roller position measurement and the roller rotation measurement.

9. The apparatus of claim 3 where a force is applied by a weight.

10. The apparatus of claim 3 wherein a force is applied by an electric, pneumatic or hydraulic actuator.

11. The apparatus of claim 3 further comprising a load cell operative to monitor a force applied to the specimen.

12. The apparatus of claim 3 further comprising a specimen chuck.

13. A material testing apparatus comprising:
   a support structure;
   at least one roller mounted on the support structure for rotational contact with a cylindrical specimen;
   a test roller mounted for rotational contact with a cylindrical specimen and for applying a radial force to said cylindrical specimen, and
   a drive system for driving one of the rollers and rotating said specimen; and
   an environmental chamber which at least partially encloses the specimen.

14. A material testing apparatus for testing the abrasion resistance characteristics of hot mix asphalt products comprising:
   a support structure;
   at least one reaction roller mounted for rotational contact with a cylindrical material specimen;
   at least one test roller for applying a force to said cylindrical specimen, and
   a rotational drive system for rotating one of said rollers to rotate said specimen while said force is applied, and a water bath.

15. The apparatus of claim 14 further comprising adjustable weights applicable to the test roller for a applying a force to the specimen.

16. The apparatus of claim 14 further comprising an actuator operative to apply a force to the test roller.

17. The apparatus of claim 14 further comprising a load cell operative to monitor a force applied to the specimen.

18. The apparatus of claim 14 further comprising a rotatable chuck for holding the specimen in contact with the reaction roller.

19. A material testing apparatus for testing the abrasion resistance characteristics of hot mix asphalt products comprising:
- a support structure;
- at least one reaction roller mounted for rotational contact with a cylindrical material specimen;
- at least one test roller for applying a force to said cylindrical specimen, and
- a rotational drive system for rotating one of said rollers to rotate said specimen while said force is applied; and
- an environmental chamber at least partially enclosing the specimen.

* * * * *